United States Patent [19]
Rheinberger et al.

[11] Patent Number: 5,393,516
[45] Date of Patent: * Feb. 28, 1995

[54] MODIFIED CHLORHEXIDINE ADDUCT

[75] Inventors: Volker Rheinberger, Vaduz, Liechtenstein; Ulrich Salz, Weissenberg, Germany; Peter Burtscher, Nützziders, Austria

[73] Assignee: Ivoclar AG, Germany

[*] Notice: The portion of the term of this patent subsequent to Apr. 19, 2011 has been disclaimed.

[21] Appl. No.: 86,919

[22] Filed: Jul. 7, 1993

[30] Foreign Application Priority Data

Jul. 8, 1992 [DE] Germany .............................. 4222821

[51] Int. Cl.$^6$ ...................... C07C 279/18; A61K 7/18; A61K 7/22; A61K 31/155
[52] U.S. Cl. ........................................ 424/52; 424/54; 514/635; 564/735
[58] Field of Search .................. 424/49–58; 514/635; 564/238

[56] References Cited

U.S. PATENT DOCUMENTS 5,098,711  12/1989  Hill et al. .
5,304,369   4/1994  Rheinberger et al. ................ 427/52

FOREIGN PATENT DOCUMENTS 2079561  4/1993  Canada .
 539811  5/1993  European Pat. Off. .
2158150  5/1972  Germany .
4135397  4/1993  Germany .

OTHER PUBLICATIONS

Chemical Abstracts, vol. 95, No. 12, Sep. 21, 1981.
Chemical Abstracts, vol. 105, No. 17, Oct. 27, 1986.
Abstract of German application DE–1–2 158 150 (May 1972).
Scheie, "Modes of Action of Currently Known Chemical Anti–Plaque Agents Other Than Chlorhexidine", J. Dent, Res. 68, (1989), pp. 1609–1616.
Gjermo, "Chlorhexidine and Related Compounds", J. Dent, Res. 68 (1989), pp. 1602–1608.
Ostela et al., "Antibacterial Activity of Dental Gels Containing Combinations of Amine Fluoride, Stannous Fluoride, Stannous Fluroide, and Chlorhexidine Against Cariogenic Bacteria", Scand J Dent Res 98, (1990) pp. 1–7.
Flotra et al., "Side Effects of Chlorhexidine Mouth Washes", Scand. J. Dent. Res. 1971, 79 pp. 119–125.
Ellingsen et al., "The Effects of Stannous and Stannic Ions on the Formation and Acidogenicity of Dental Plaque in vivo", Acta Odontol. Scand. 38, (1980) pp. 219–222.
Tinanoff et al., "The Effect of NaF and SnF$_2$ Mouthrinses on Bacterial Colonization of Tooth Enamel: TEM and SEM Studies", Caries Res. 10 (1976) pp. 415–426.
Ellingsen, "Scanning Electron Microscope and Electron Microprobe Study of Reactions of Stannous Fluoride and Stannous Chloride With Dental Enamel", J. Dent. Res. 94, (1986), pp. 299–305.
Ellingsen et al., "Treatment of Dentin With Stannous Fluoride – SEM and Electron Microprobe Study", Scand, J. Dent, Res. 95 (1987) pp. 281–286.

Primary Examiner—Shep K. Rose
Attorney, Agent, or Firm—Cushman, Darby & Cushman

[57] ABSTRACT

A chlorhexidine adduct is described, which comprises one molecule of chlorhexidine with three molecules of hydrogen fluoride and one molecule of hydrogen tin trifluoride. The adduct displays a high antibacterial effectiveness against Streptococcus mutans even in very low concentrations.

10 Claims, 4 Drawing Sheets

MODIFIED CHLORHEXIDINE ADDUCT

BACKGROUND OF THE INVENTION

1. Technical Field

The invention relates to a chlorhexidine adduct which can be used as an antiseptic and in particular as an antiseptic in dentistry as well as a therapeutic and prophylactic anti-plaque agent.

BACKGROUND INFORMATION

In the attempt to inhibit or completely stop the formation of plaque and therefore also of caries, the effectiveness of substances with antibacterial properties such as chlorinated phenols, formaldehyde and quaternary ammonium compounds has been tested in the past. However, these compounds have not been introduced into practice in view of their toxicity and their limited action spectrum.

The most effective anti-plaque agent at present is chlorhexidine (1,6-bis-($N^5$-P-chlorophenyl-N'-diguanidino)-hexane) which is used particularly in the form of the water-soluble digluconate and also as the sparingly soluble diacetate and dihydrochloride (cf. A.Scheie in J. Dent. Res. 68, 1609 (1989) and P. Gjermo in J. Dent. Res. 68, 1602 (1989)).

Apart from these chlorhexidine compounds, chlorhexidine dihydrofluoride is also known which, according to DE-OS 21 58 150, is used as an antiseptic agent in transparent tooth gels.

Moreover, a mixture of chlorhexidine, amine fluoride and tin difluoride is known from I. Ostela and J. Tenovuo in Scand. J. Dent. Res. 98, 1 (1990). This mixture can be used in tooth gels as a bactericide against cariogenic bacteria.

Applicants' prior copending application Ser. No. 965,019, filed Oct. 23, 1992, now U.S. Pat. No. 5,304,369, describes and claims a chlorhexidine adduct comprising one mole of chlorhexidine with six moles of hydrogen fluoride.

It has been shown that by using chlorhexidine as a chemotherapeutic, bacteria of the type Streptococcus mutans can be countered effectively. Bacteria of this type play an essential role in the formation of caries on human teeth. It is therefore assumed that by reducing their quantity on the surface of teeth, the formation of caries can be effectively prevented (cf. I. Ostela and J. Tenovuo in Scand. J. Dent. Res. 98, 1 (1990)).

The bactericidal action which chlorhexidine exerts against bacteria of the type Streptococcus mutans is, however, severely weakened if it is used in low concentrations. Even chlorhexidine is, therefore, subject to significant limitations in practical applications where reducing the amount of tooth plaque is important, which otherwise can lead to the formation of parodontosis and caries. Furthermore, the use of chlorhexidine in higher concentrations can result in undesirable discolorations of the tongue, teeth, prostheses and fillings (cf. L. Flötra, P. Gjermo, G. Rölla and J. Waerhaug in Scand. J. Dent. Res. 79, 119 (1971)).

Tin ions show a significant anti-caries action and a plaque-inhibiting effect. Firstly, the metabolism of the microorganisms present in the plaque is disrupted (see e.g. J.E. Ellingsen, B. Svatun and G. Rölla, Acta Odontol. Scand. 38, 219 (1980) and N. Tinanoff, J.M. Brady and A. Gross, Caries Res. 10, 415 (1976)), and, secondly, tin (II) ions are deposited on the surface of the tooth and form acid-resistant precipitates there, together with fluoride, calcium and phosphate ions (see e.g. J.E. Ellingsen, Scand. J. Dent. Res..94, 229 (1986) and J.E. Ellingsen and G. Rölla, Scand. J. Dent. Res. 95, 281 (1987)).

SUMMARY OF THE INVENTION

It is therefore the object of the invention to provide a chlorhexidine adduct which, as an anti-plaque agent, effectively counters the formation and growth of tooth plaque even in very low concentrations, which can desensitize sensitive tooth necks and moreover which, through fluoride release, is capable of protecting the tooth enamel against demoralization, particularly demineralisation by acids.

This object is surprisingly achieved by the chlorhexidine adduct according to claim 1 and the process for its production according to claims 2, 3 and 4 and its use according to claims 5 and 6.

DETAILED DESCRIPTION OF THE INVENTION

The chlorhexidine adduct according to the invention is a compound of the following formula:

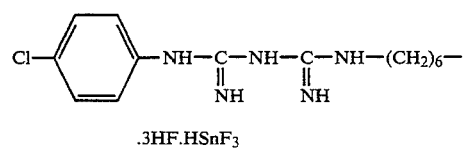

.3HF.HSnF$_3$

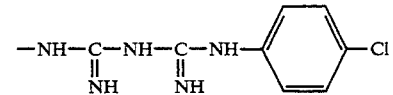

or its hydrates.

The adduct displays the IR spectrum according to FIG. 1. The exact molecular structure of the adduct according to the invention is not known. Basically, it is possible that the adduct according to the invention consists of electrically neutral molecules or is present in the form of ions and hence as a salt.

The adduct according to the invention is produced by reacting a chlorhexidine salt (preferably chlorhexidine digluconate), tin difluoride and hydrogen fluoride in a molar ratio of 1:1 to 4:4 to 8 in a mixture of 3:1 parts by volume ethanol/water as solvent and separating the precipitate formed.

The chlorhexidine according to the invention is preferably prepared by carrying out the reaction at room temperature with a chlorhexidine salt to tin difluoride to hydrogen fluoride molar ratio of 1:4:6. The yields thus obtainable are 90 to almost 100%.

Increased temperatures are disadvantageous when carrying out the production process since they promote the formation of mixed products with a lower tin fluoride content.

A reaction time of 24 hours is usually sufficient to achieve a complete reaction. The reaction time can, however, vary depending on the reaction parameters selected. The best-suited reaction time for the case in question can, however, be determined easily by routine experiments.

The chlorhexidine adduct formed by the reaction predominantly as precipitate is removed and purified, preferably by filtration and subsequent washing with water and acetone. By working-up of the mother liquors, further chlorhexidine adduct can be obtained, so that overall yields of 90 to almost 100% are obtainable. The purified product is then dried in a conventional way and afterwards exists in the form of hydrates with varying levels of water, depending on the degree of drying.

Because of its strong antibacterial action, the chlorhexidine adduct according to the invention can be used as a therapeutic or prophylactic anti-plaque agent. In doing so, it prevents the formation of plaque and inhibits the growth of films already present on the tooth. Diseases which are caused by the presence of plaque, such as parodontosis, caries and gingivitis, are therefore able to be tackled effectively with the chlorhexidine adduct according to the invention. Furthermore, it can contribute to the desensitizing of sensitive tooth necks. It is preferably used in dental materials, such as tooth varnishes, fissure sealants, prophylactic pastes, mouthwashes, toothpicks, dental floss, dental chewing-gum, wound dressings, dental creams, gingiva trainers, disinfectants for protheses and impression materials, drying agents, under-filling materials, cements, filling materials, adhesives and endodontic materials. The adduct according to the invention can be deposited on a solid substrate, such as a toothpick or dental floss, or incorporated into dental materials, such as provisional filling materials and fissure sealants.

Of particular advantage is the incorporation of the adduct according to the invention in dental materials which are to remain in the oral cavity for a limited period of time, such as provisional filling materials, wound dressings, impression materials and temporary cements. If the adduct according to the invention is incorporated for example into a provisional filling material, one obtains, after its removal, a germ-free cavity into which the final filling can immediately afterwards be placed.

Since the chlorhexidine adduct is only very slightly soluble in common solvents, it is preferably incorporated into the said dental materials as a solid. It is added to the dental materials in quantities of 0.1 to 20 wt. %, preferably 1 to 10 wt. % and particularly preferably 3 to 7 wt. %, relative to the total weight of the material. Examples of suitable dental materials are those which contain 10 to 95 wt. % polymerisable organic binder, 5 to 90 wt. % inorganic and/or organic fillers and 0.01 to 5 wt. % catalysts, relative to the weight of the total material.

Furthermore, solutions containing 0.03 to 0.001 wt. % of the adduct according to the invention can be used. Suitable as solvents are e.g. water, ethanol, acetone, ethyl acetate, triethylene glycol dimethacrylate and decanediol dimethacrylate. Further, synthetic or natural resins can be used which are soluble in common solvents and become hard after evaporation of the solvent. Examples for such resins are shellac, benzoin resin, polyvinyl pyrrolidone and colophony.

A further preferred application of the chlorhexidine adduct is that as a therapeutic or prophylactic anti-plaque agent. It prevents the formation of plaque and inhibits the growth of plaque already present. Diseases which are caused by the presence of plaque, e.g. parodontosis, primary and secondary caries and gingivitis, can therefore be combatted effectively with the chlorhexidine adduct according to the invention.

As regards its bactericidal effectiveness, the chlorhexidine adduct according to the invention is fully comparable in a concentration of 0.03 wt. % with chlorhexidine, which at present is regarded as the most effective anti-plaque agent. Surprisingly, however, the effectiveness of chlorhexidine is significantly surpassed if both are used in concentrations less than or equal to 0.01 wt. %. In this concentration range, the chlorhexidine adduct according to the invention is even clearly superior to tin difluoride, a compound known to have very good bactericidal properties.

The superiority of the adduct according to the invention especially in low concentrations is of particular significance for practical applications. For, as a result of the permanent salivation in the oral cavity, the active ingredients used are continuously diluted. An active ingredient, such as the chlorhexidine adduct according to the invention, which shows a strong bactericidal effect even in low concentrations, is therefore of particular advantage.

Finally, the high fluorine content of the adduct according to the invention means that it can effect hardening of the tooth enamel through fluoridization and therefore can also effectively protect against the formation of caries in this respect. The adduct according to the invention further shows the aforementioned effect of tin ions.

The adduct according to the invention can be worked in or applied on dental materials such as inter alia the aforementioned filling compositions, dental varnishes, fissure sealants, prophylactic pastes, tooth-picks, dental floss, dental chewing-gum, wound dressings, dental creams, gingiva trainers, disinfectants for protheses and impression materials, drying agents, under-filling materials, cements, filling materials, adhesives and endodontic materials, or applied on the teeth in the form of many different dental treatment agents, such as toothpastes, tooth gels, tooth varnishes or mouth rinses.

The invention is described in more detail in the following examples.

EXAMPLE 1

To produce the chlorhexidine adduct according to the invention, 480 ml ethanol/water (3:1) were introduced first and 12.6 g (0.08 mole) tin difluoride and 6 g of a 40% HF solution (0.12 mole) dissolved therein. 85 ml (corresponding to 90 g) (0.02 mole) of an aqueous 20% chlorhexidine digluconate solution were added dropwise with stirring within an hour. After a further 5 hours stirring, the precipitate formed was filtered off and washed three times with 50 ml ethanol/water (3:1). Further product crystallized out from the mother liquor within a week. Drying of the precipitate obtained was carried out in the drying cupboard at 50° C. The yield of adduct was almost quantitative.

Figure 1:
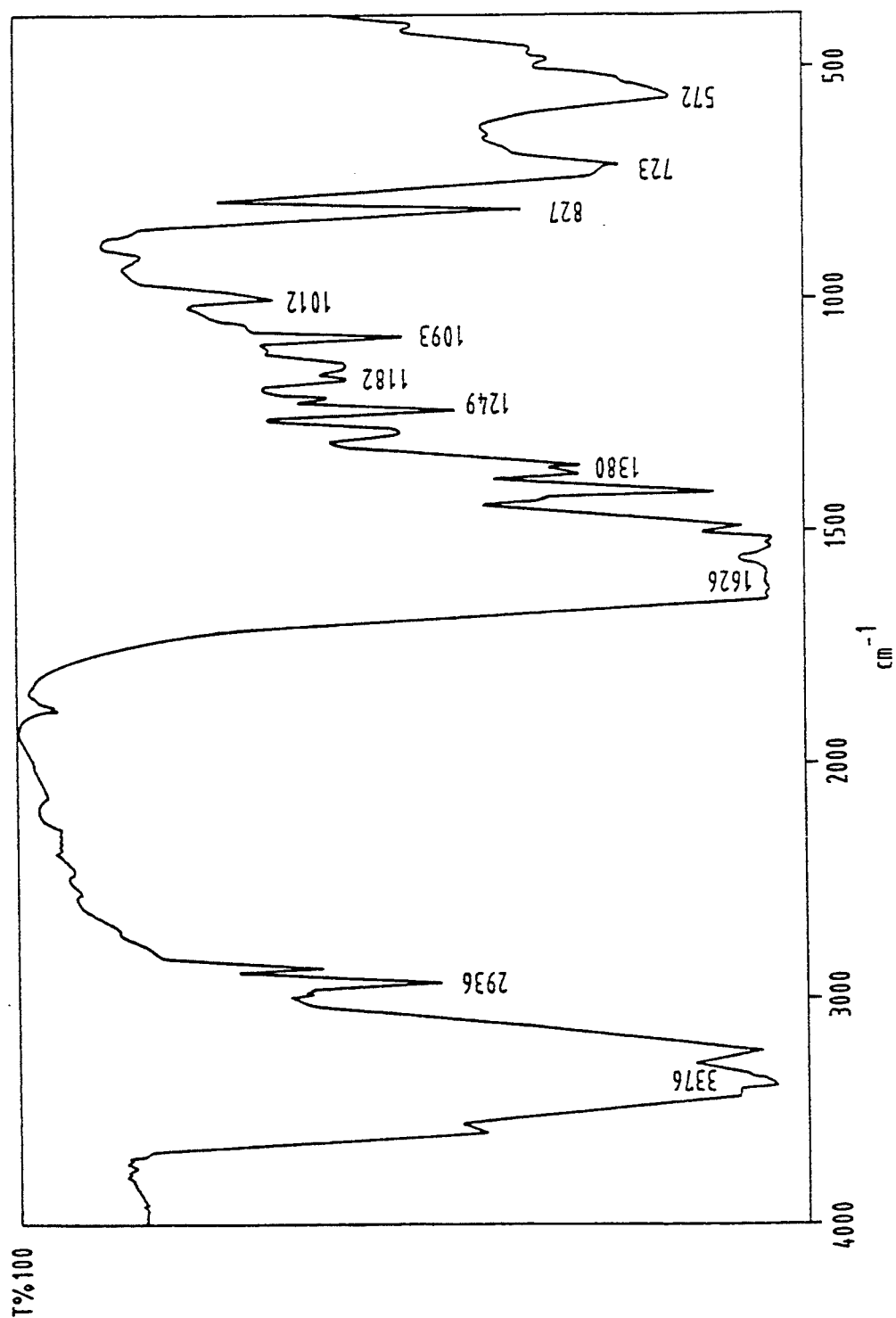
FIG. 1 reproduces the 1R spectrum (K Br pressed disk).

The IR spectrum (KBr pressed disk) is reproduced in FIG. 1.

The elementary analysis shows that the product is chlorhexidine trihydrofluoride-hydrogen tin trifluoride with 2 moles crystal water.

| $C_{22}H_{30}N_{10}Cl_2.3$ HF.HSnF$_3$.2 H$_2$O MW = 778.2 Elementary analysis: | | |
|---|---|---|
|  | found | theoretical |
| C | 34.48% | 33.96% |
| H | 4.56% | 4.40% |
| N | 18.02% | 18.00% |
| Cl | 9.06% | 9.11% |
| F | 14.58% | 14.65% |
| Sn | 14.45% | 15.25% |
| H$_2$O*) | 4.84% | 4.63% |

*)H$_2$O content determined by the Karl Fischer method
(Note: The theoretical value of 15.25% for tin is not achieved in the elementary analysis since chlorhexidine hexahydrofluoride forms as a by-product during the synthesis in a yield of about 5%. The value for tin therefore falls, whilst a higher value is measured for carbon.)
Solubility:
Water 0.03 wt. %
Ethanol 0.02 wt. %

EXAMPLE 2

The antibacterial effectiveness of the chlorhexidine adduct according to the invention was demonstrated in the agar-diffusion test with Streptococcus mutans.

For this, culture suspensions of Streptococcus mutans were introduced in liquid yeast-extract-dextrose-agar. After solidification of the agar plates, a basin of 10 mm diameter was cut out. Into this were poured 0.1 ml of the respective test solution. The samples were prepared in duplicate in each case and the diameters of the zones of inhibition were measured after 24 hour incubation at 37° C. The results of these tests are set out in the following Table I.

TABLE I

| | Inhibition zone diameters | | |
|---|---|---|---|
| Concentration | Solution A | Solution B | Solution C |
| 0.03 wt. % | 17 mm | 16 mm | 20 mm |
| 0.01 wt. % | 13 mm | 15 mm | 11 mm |
| 0.003 wt. % | 11 mm | 11 mm | 10 mm* |

*no effectiveness
Solution A: Aqueous solution of chlorhexidine digluconate
Solution B: Aqueous solution of the chlorhexidine adduct according to the invention
Solution C: Aqueous solution of tin difluoride The test result show that at a concentration of 0.03 wt. % the antibacterial effectiveness of the chlorhexidine adduct according to the invention against Streptococcus mutans is comparable with that of chlorhexidine digluconate, whilst tin difluoride displays an even stronger action at this concentration. With increasing dilution, however, the effectiveness of the known compounds falls sharply, in the case of tin difluoride at a concentration of 0.003 wt. % even to the extent that an anti-bacterial effect can no longer be detected. In contrast to this, the antibacterial effectiveness of the adduct according to the invention is still very high even at concentrations of 0.01 to 0.003 wt. %. Its superiority especially at low concentrations thus makes it a very effective anti-plaque agent.

EXAMPLE 3

A dental material as described in Example 4 was deposited in a layer of ca. 2 mm on the surface of an absolutely plane-parallel, tin-free hydroxyl-apatite testpiece and polymerized for 40 seconds with the Heliomat ® (light apparatus from Vivadent). Afterwards, the thus-coated testpiece was stored for 12 hours at 37° C. in distilled water. The polymerized on layer was then removed with microscopic control and the tin content on the hydroxyl apatite surface was analyzed by means of SIMS (secondary ions mass spectrometry). This analysis process is described in Caries Res. 20, 419 (1986).

Figure 2:
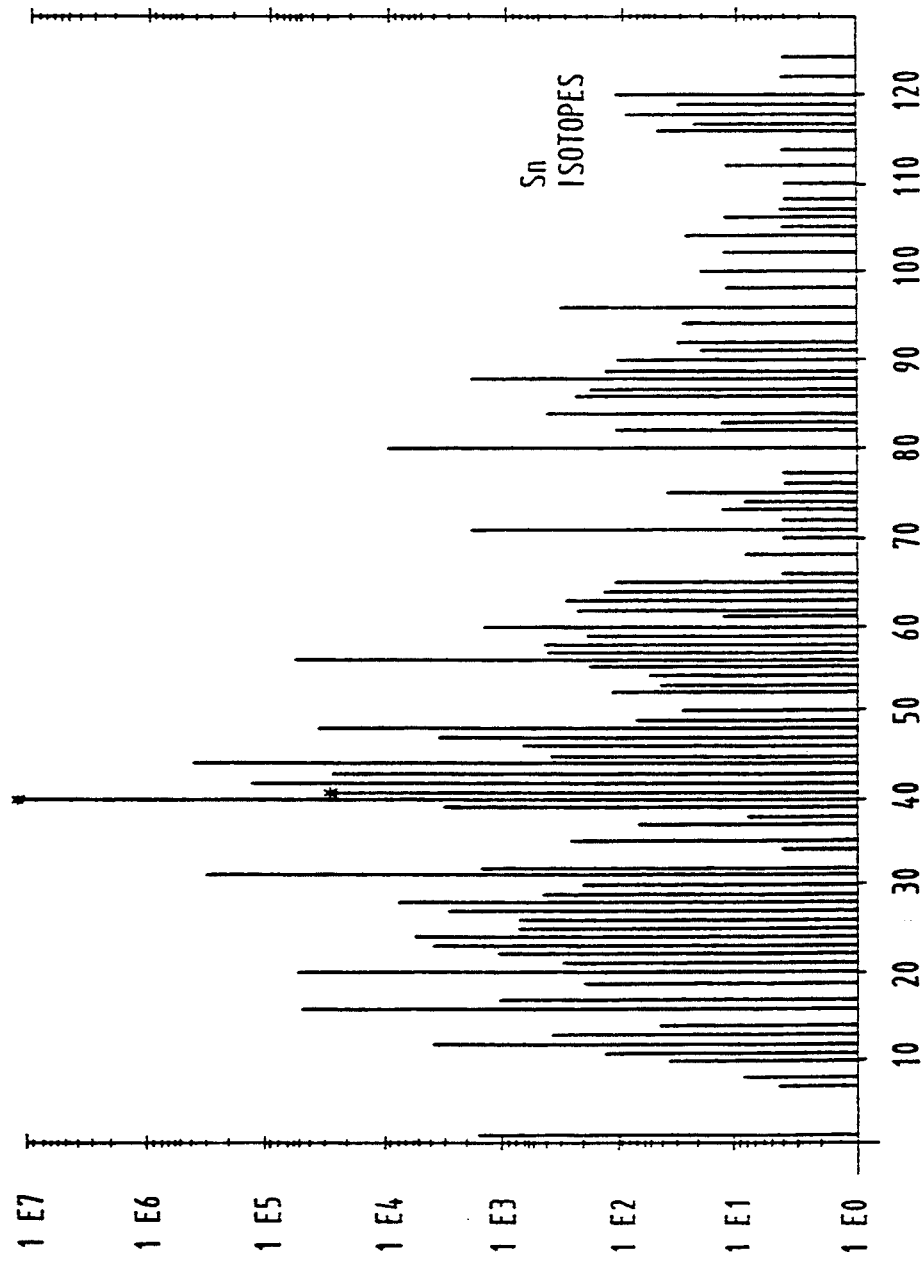
FIG. 2 shows dental material tin deposited on hydroxyl apatite surface.

The result obtained is depicted in FIG. 2 and shows that a considerable portion of the tin present in the dental material was deposited on the surface of the hydroxyl apatite.

EXAMPLE 4

A light-curing fissure sealant contains the following components:

| | |
|---|---|
| 56.08 wt. % | Bis-phenol A-glycidyl methacrylate (Bis-GMA) |
| 36.1 wt. % | Triethylene glycol dimethacrylate |
| 0.45 wt. % | Cyanoethylmethyl aniline |
| 0.25 wt. % | DL-camphor quinone |
| 2.1 wt. % | TiO$_2$ |
| 0.02 wt. % | 2,6-di-tert.-butyl-p-cresol |
| 5.0 wt. % | Chlorhexidine adduct |

The light-curable fissure sealant was obtained by mixing all the components. This was applied with a paint-brush onto the fissures of a molar and cured for 20 sec with the Heliolux ® light-curing apparatus from Vivadent/Liechtenstein. The fissures were sealed permanently in this way and, through the fluoride release of the chlorhexidine adduct incorporated in the sealant, excellent caries protection was obtained in the occlusal region.

By admixing 1 to 5 wt. % of the chlorhexidine adduct to the fissure sealant basic formulation, no reduction in the degree of through-hardening was observed, as the following values for Vickers hardness show:

| | HV 0.5 |
|---|---|
| Fissure sealant without chlorhexidine adduct | 188 MPa |
| Fissure sealant + 1% chlorhexidine adduct | 203 MPa |
| Fissure sealant + 3% chlorhexidine adduct | 211 MPa |
| Fissure sealant + 5% chlorhexidine adduct | 184 MPa |

To demonstrate the chlorhexidine and fluoride migration, 10 testpieces each with a diameter of 50 mm and a height of 0.5 mm were stored in dist. water at 37° C. The concentration of fluoride ions was determined using a fluoro-electrode, and the chlorhexidine concentration was measured by means of UV-spectroscopy. The results are set out below in Table II.

TABLE II

| Cumulative fluoride and chlorhexidine release | | |
|---|---|---|
| Migration time [days] | Fluoride release [μm/cm$^2$] | Chlorhexidine release [μg/cm$^2$] |
| 1 | 1.26 | 4.30 |
| 2 | 1.97 | 5.41 |
| 3 | 2.61 | 5.96 |
| 4 | 3.13 | 6.36 |
| 7 | 4.57 | 7.11 |
| 10 | 5.77 | 8.37 |
| 17 | 8.01 | 9.07 |
| 24 | 9.83 | 9.77 |
| 30 | 11.21 | 10.37 |
| 44 | 13.87 | 10.93 |
| 86 | 18.49 | 11.01 |
| 149 | 22.91 | 11.09 |

Figure 3:
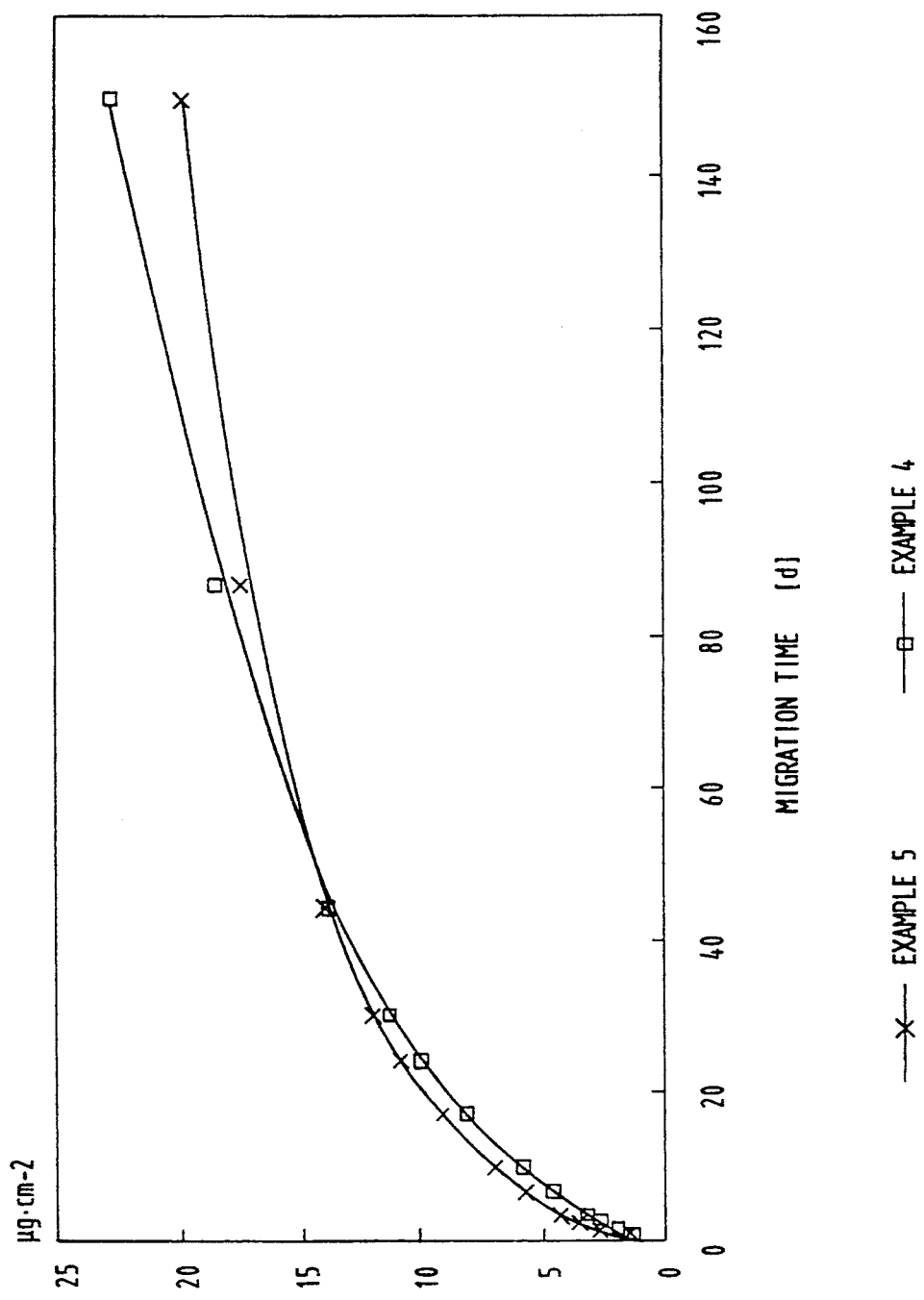
FIGS. 3 and 4 graphically represent cumulative fluoride and chlorhexidine release migration time, in days.
Figure 4:
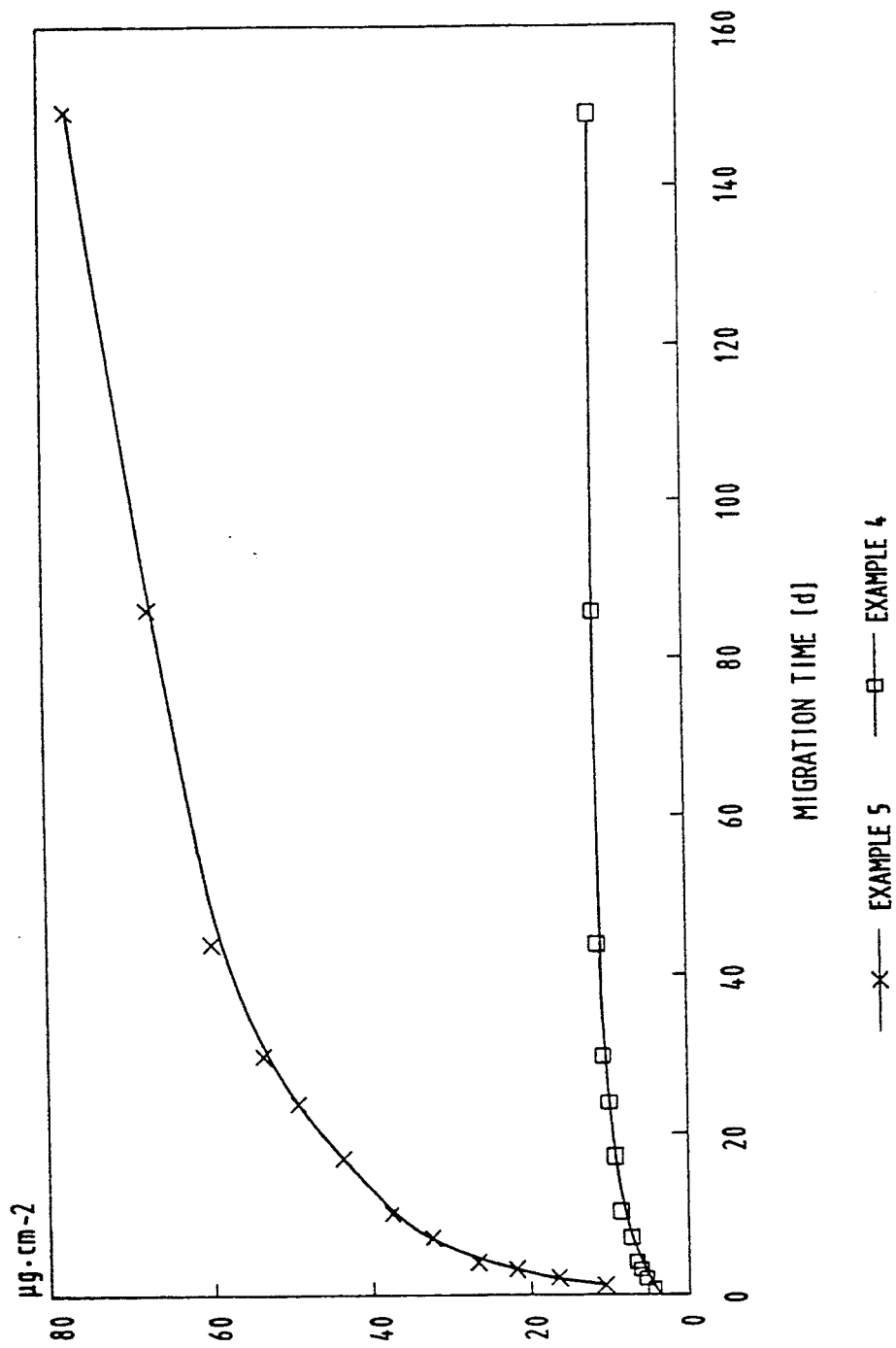

The results are represented graphically in FIGS. 3 and 4.

EXAMPLE 5

A light-curing dental plastic with relatively high water absorption and therefore high active ingredient release (e.g. suitable as provisional filling material or as a wound dressing) has the following composition:

| | |
|---|---|
| 41.4 wt. % | polyester urethane dimethacrylate |
| 0.25 wt. % | cyanoethylmethyl aniline |
| 0.15 wt. % | DL-camphor quinone |
| 0.02 wt. % | 2,6-di-tert.-butyl-p-cresol |
| 33.25 wt. % | splinter polymerisate |
| 19.93 wt. % | finely-dispersed silanised $SiO_2$ |
| 5.0 wt. % | chlorhexidine adduct |

The splinter polymerisate consists of:

| | |
|---|---|
| 59.4% | urethane dimethacrylate |
| 40% | finely dispersed silanised $SiO_2$ |
| 0.6% | benzpinacol |

These components are mixed together and polymerized at 120° C. The filled polymerisate is ground to a polymer powder. The amorphous finely-dispersed silanised $SiO_2$ is Aerosil® OX 50 from Degussa AG.

A light-curing dental material was obtained by mixing all the components.

The water absorption of dental filling composites normally lies in the region of 1 wt.%. However, this material shows a water absorption in the region of 3 wt.% (3 weeks $H_2O$ storage at 37° C.).

Chlorhexidine and fluoride migration:

The cumulative fluoride and chlorhexidine release is summarized in the following table III.

TABLE III

| Migration time [days] | Fluoride release [μm/cm²] | Chlorhexidine release [μm/cm²] |
|---|---|---|
| 1 | 1.67 | 10.4 |
| 2 | 2.64 | 16.3 |
| 3 | 3.52 | 21.7 |
| 4 | 4.29 | 26.5 |
| 7 | 5.64 | 32.1 |
| 10 | 6.87 | 37.3 |
| 17 | 8.97 | 43.5 |
| 24 | 10.72 | 49.3 |
| 30 | 11.92 | 53.5 |
| 44 | 14.02 | 59.8 |
| 86 | 17.38 | 67.3 |
| 149 | 19.90 | 76.8 |

The results are represented graphically in FIGS. 3 and 4.

Microbiological action

As the migration experiments show, significant quantities of fluoride and chlorhexidine are released from this dental material, so that even in this combination a sufficient inhibition of the growth of microorganisms is to be expected.

Since not all microorganisms react equally on released active ingredients, investigations were conducted using the following microbes.

| | |
|---|---|
| Gram-positive bacteria: | *Streptococcus mutans* |
| | *Staphylococcus aureus* |
| Gram-negative bacteria: | *Pseudomonas auruginosa* |
| | *Escherichia coli* |
| Fungus: | *Candida albicans* |

Testpieces (d=10 mm, h=2 mm) were introduced into the moist microorganism cultures at 37° C. over a period of 24 hours and then the zone of inhibition was determined.

| | Zone of inhibition diameter [mm] |
|---|---|
| *Streptococcus mutans* | 13 |
| *Staphylococcus aureus* | 14 |
| *Pseudomonas auruginosa* | 16 |
| *Escherichia coli* | 14 |
| *Candida albicans* | 10 (no effect) |

With the exception of *Candida albicans*, a clear inhibition of growth in these various microorganisms is detectable.

We claim:

1. Chlorhexidine adduct with the following formula

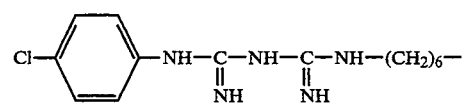

.3HF.HSnF₃

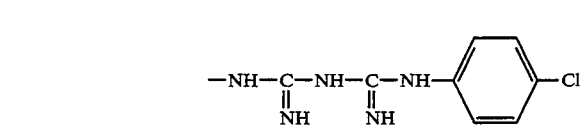

or its hydrates.

2. A process for preparing the chlorhexidine adduct according to claim 1 comprising:
   a) reacting a chlorhexidine salt, tin difluoride and hydrogen fluoride in a molar ratio of 1:1 to 4:4 to 8 in a mixture of 3:1 parts by volume ethanol/water as solvent, and
   b) separating the resulting precipitate.

3. A process according to claim 2 comprising:
   a) reacting the chlorhexidine salt, tin difluoride and hydrogen fluoride in a molar ratio of 1:4:6 and
   b) carrying out step a) at room temperature.

4. A process according to claim 2 or 3, wherein chlorhexidine digluconate is used as said chlorhexidine salt.

5. An antiseptic composition comprising the chlorhexidine adduct or its hydrates according to claim 1 as an antiseptic.

6. A dental material comprising the chlorhexidine adduct or its hydrates according to claim 1 as an agent for the prevention of caries.

7. A dental material comprising:
   10-95 wt. % polymerisable organic binder;
   5-90 wt. % inorganic or organic fillers;
   0.01-5 wt. % catalyst; and
   0.1-20 wt. % of a chlorohexidine adduct comprising the following formula:

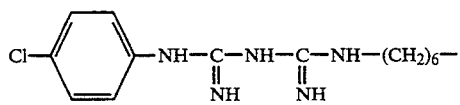

.3HF.HSnF$_3$

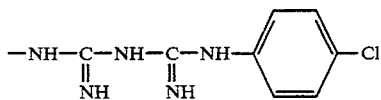

or its hydrates.

8. The dental material according to claim 7, wherein said chlorohexidine adduct is present in an amount of 1-10 wt. %.

9. The dental material according to claim 7, wherein said chlorohexidine adduct is present in an amount of 3-7 wt. %.

10. An antiseptic comprising:
0.03–0.001 wt. % of a chlorohexidine adduct comprising the following formula:

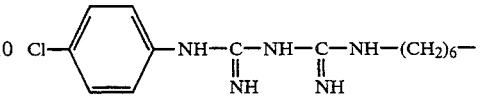

.3HF.HSnF$_3$ or its hydrates; and
a solvent.

* * * * *